(12) United States Patent
Kim et al.

(10) Patent No.: US 11,458,305 B2
(45) Date of Patent: Oct. 4, 2022

(54) DEVICE FOR INSERTING NEURAL PROBES

(71) Applicant: KOREA INSTITUTE OF SCIENCE AND TECHNOLOGY, Seoul (KR)

(72) Inventors: Jinseok Kim, Seoul (KR); Jong Woong Park, Seoul (KR); Hyungdal Park, Seoul (KR); Wonsuk Choi, Seoul (KR); Ockchul Kim, Seoul (KR); Woo Hyun Jung, Seoul (KR); Sunyoung Jung, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 1151 days.

(21) Appl. No.: 15/886,913

(22) Filed: Feb. 2, 2018

(65) Prior Publication Data

US 2018/0221653 A1 Aug. 9, 2018

(30) Foreign Application Priority Data

Feb. 9, 2017 (KR) .......................... 10-2017-0018325

(51) Int. Cl.
*A61N 1/05* (2006.01)
*A61B 5/00* (2006.01)
(Continued)

(52) U.S. Cl.
CPC .............. *A61N 1/0556* (2013.01); *A61B 5/24* (2021.01); *A61B 5/4041* (2013.01);
(Continued)

(58) Field of Classification Search
CPC ................ A61N 1/0556; A61N 1/0558; A61B 5/04001; A61B 5/4041; A61B 2017/2931;
(Continued)

(56) References Cited

U.S. PATENT DOCUMENTS

| 5,400,784 A * | 3/1995 | Durand ................ A61N 1/0556 29/825 |
| 2007/0106143 A1* | 5/2007 | Flaherty ............... A61N 1/0529 600/373 |

(Continued)

FOREIGN PATENT DOCUMENTS

| KR | 10-2012-0052634 A | 5/2012 |
| KR | 10-1158775 B1 | 6/2012 |

(Continued)

OTHER PUBLICATIONS

Miguel A. L. Nicolelis et al., "Chronic, multisite, multielectrode recordings in macaque monkeys", PNAS, Sep. 16, 2003, pp. 11041-11046, vol. 100, No. 19.

(Continued)

*Primary Examiner* — Eun Hwa Kim
*Assistant Examiner* — Catherine C. Premraj
(74) *Attorney, Agent, or Firm* — Rabin & Berdo, P.C.

(57) ABSTRACT

A probe insertion device for a neural probe structure with a plurality of probes to simultaneously insert the plurality of probes into a nerve includes a nerve holder to fix the nerve surrounding an outer circumference of the nerve, and a probe holder positioned outside in a radial direction of the nerve holder to fixedly support the probes surrounding a circumference of the nerve holder. The probe holder includes a plurality of sections ("probe holder sections") arranged radially with respect to the nerve holder and moveable in a radial direction of the nerve holder, and the plurality of probe holder sections simultaneously moves the plurality of probes toward the nerve holder having fixed the nerve, so that the plurality of probes is simultaneously inserted into the nerve in a radial shape when viewed in a lengthwise direction of the nerve.

13 Claims, 18 Drawing Sheets

(51) Int. Cl.
  *A61B 5/24* (2021.01)
  *A61B 17/29* (2006.01)
(52) U.S. Cl.
  CPC ............ *A61B 2017/2931* (2013.01); *A61B 2017/2945* (2013.01); *A61B 2560/063* (2013.01); *A61B 2562/0209* (2013.01); *A61N 1/0558* (2013.01)
(58) Field of Classification Search
  CPC ...... A61B 2017/2945; A61B 2560/063; A61B 2562/0209; A61B 5/24
  See application file for complete search history.

(56) References Cited

U.S. PATENT DOCUMENTS

| | | | |
|---|---|---|---|
| 2014/0228738 A1* | 8/2014 | Park | A61L 31/16 604/20 |
| 2017/0020403 A1 | 1/2017 | Kim et al. | |

FOREIGN PATENT DOCUMENTS

| | | |
|---|---|---|
| KR | 10-2016-0051016 A | 5/2016 |
| KR | 10-1700886 B1 | 2/2017 |

OTHER PUBLICATIONS

Patrick J. Rousche et al., "Chronic recording capability of the Utah Intracortical Electrode Array in cat sensory cortex", Journal of Neuroscience Methods, 1998, pp. 1-15, vol. 82.
Patrick J. Rousche et al., "A Method of Pneumatically Inserting an Array of Penetrating Electrodes into Cortical Tissue", Annals of Biomedical Engineering, 1992, pp. 413-422, vol. 20.
Po-Cheng Chen et al., "Detachable Ultrasonic Enabled Inserter for Neural Probe Insertion Using Biodissolvable Polyethylene Glycol", Transducers, Jun. 21-25, 2015, pp. 125-128.
Rio J. Vetter et al., "Chronic Neural Recording Using Silicon-Substrate Microelectrode Arrays Implanted in Cerebral Cortex", IEEE Transactions on Biomedical Engineering, Jun. 2004, pp. 896-904, vol. 51, No. 6.

* cited by examiner

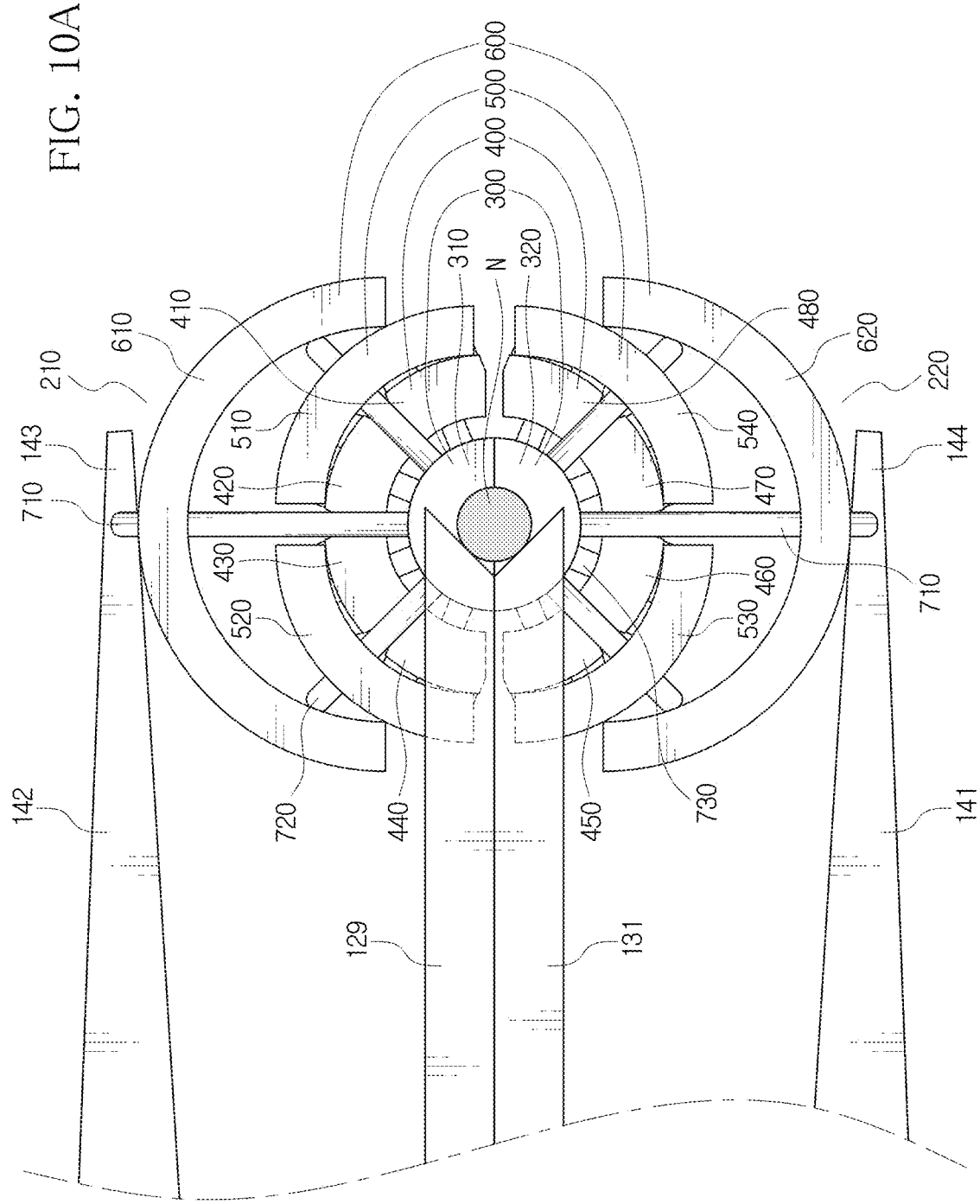

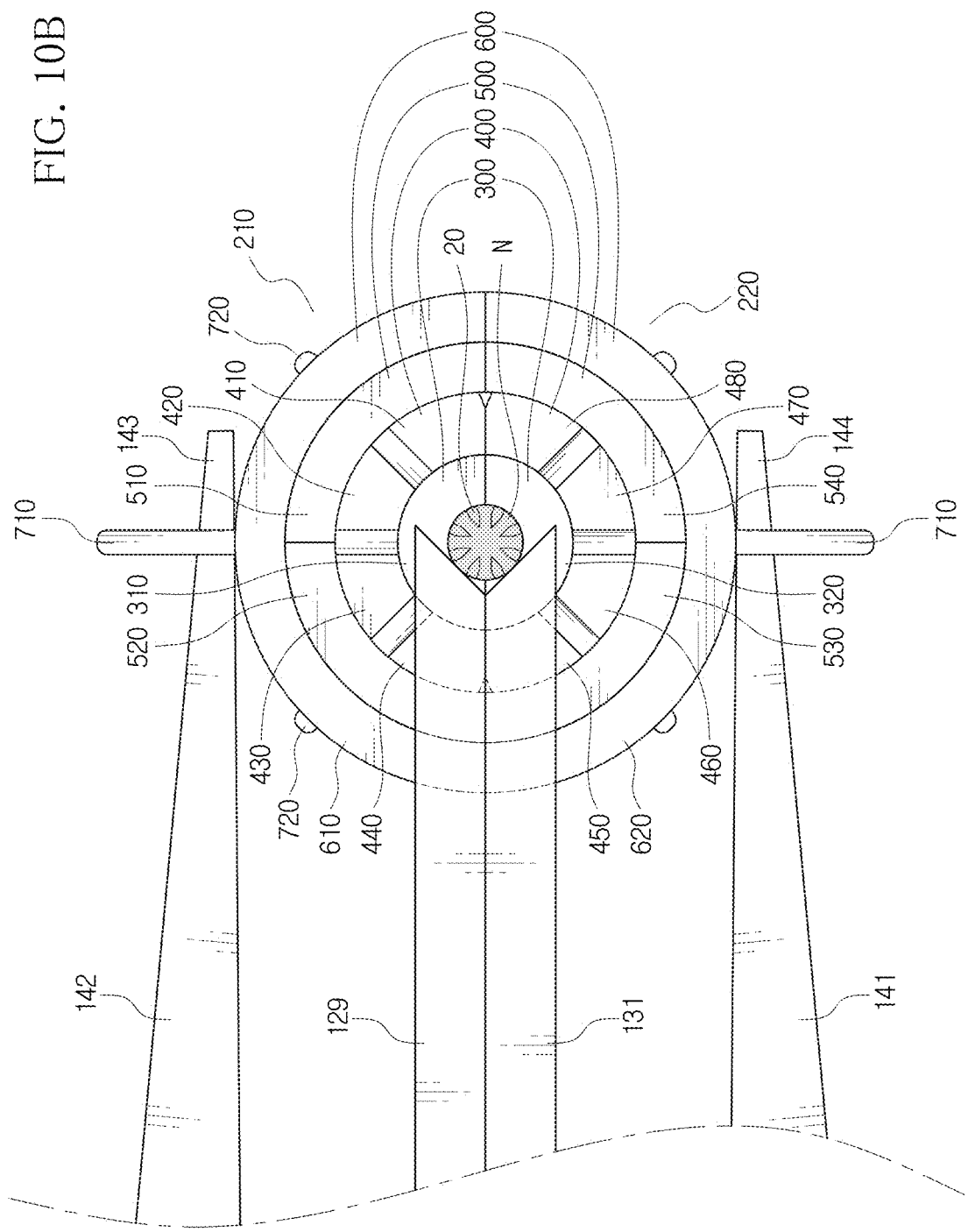

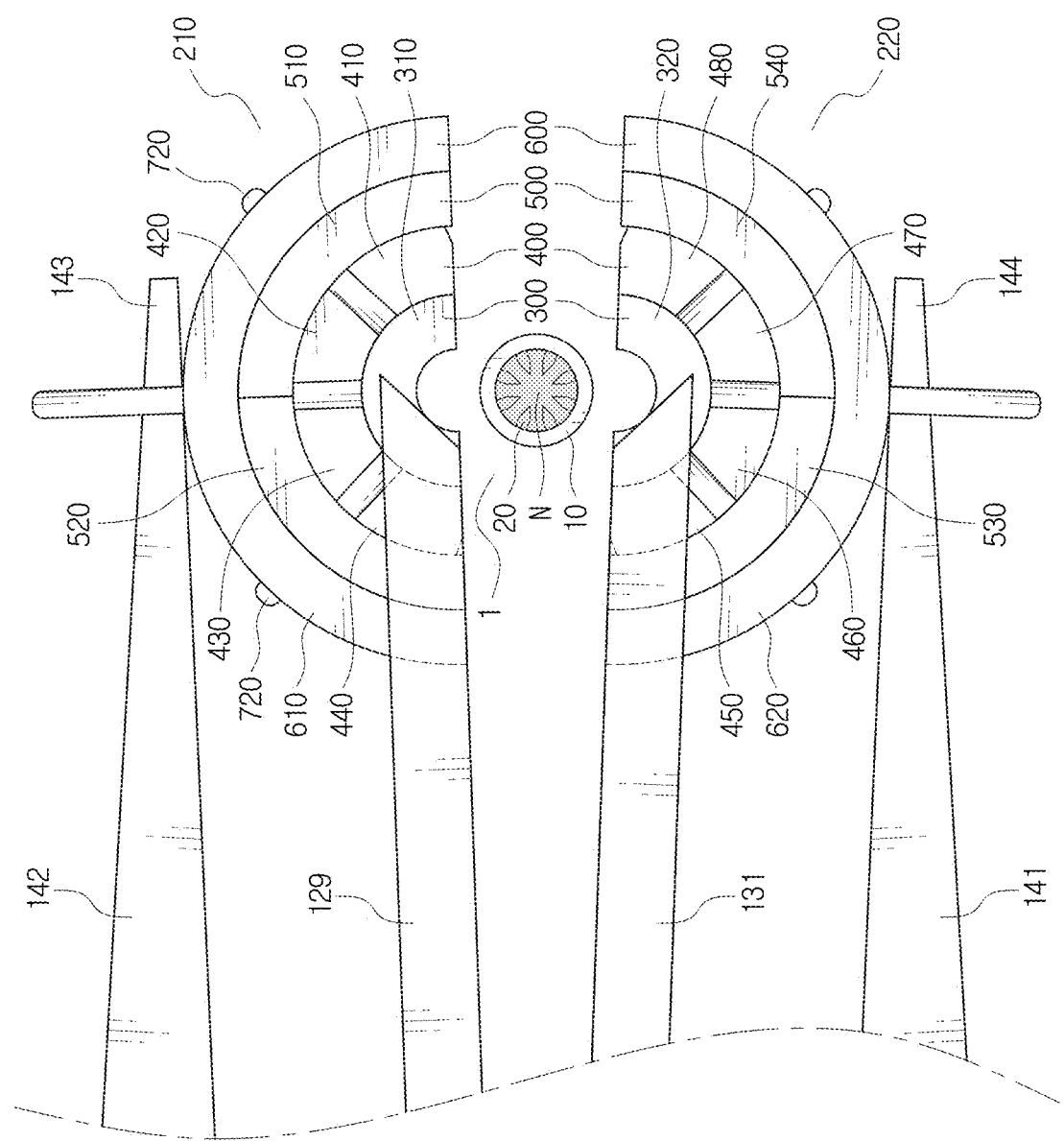

DEVICE FOR INSERTING NEURAL PROBES

DESCRIPTION OF GOVERNMENT-SPONSORED RESEARCH AND DEVELOPMENT

This study was supported by STEAM research project (Development of multichannel, high selectivity biocompatible two-way neural electrode for long-term implantation, Project No. 1711042912) of National Research Foundation of Korea, Ministry of Science, ICT and Future Planning, affiliated with Korea Institute of Science and Technology.

CROSS-REFERENCE TO RELATED APPLICATION

This application claims priority to Korean Patent Application No. 10-2017-0018325, filed on Feb. 9, 2017, and all the benefits accruing therefrom under 35 U.S.C. § 119, the contents of which in its entirety are herein incorporated by reference.

BACKGROUND

1. Field

The present disclosure relates to a device for inserting neural probes, and more particularly, to a probe insertion device for assisting the installation of a neural probe structure with a plurality of probes so that the plurality of probes is easily inserted into nerve.

2. Description of the Related Art

Recently, as neural interfaces for neuroprosthetic or human-machine interface (HMI) applications, studies are being made on an neural electrode structure that is directly connected to the nerve to apply stimulation to the nerve or collect neural signal information from the nerve.

An example of the neural electrode structure is cuff electrodes including a body of a flexible material having a wide area and electrodes embedded in the body. The cuff electrode uses a method that wraps and fixes the flexible body around the entire surface of the nerve like rolling a bandage and detects neural signals through the electrodes formed on the body surface.

However, in the cuff electrode, because the body is fixed such that the body wraps up the outer circumferential surface of nerve, part of the nerve is compressed, which impedes the blood flow in the blood vessels of epineurium, causing chronic pain. Additionally, the body generally made of a polymer material disallows oxygen and water to permeate, causing pain or necrosis of the nerve at a part on which the body is worn. Therefore, it is difficult to implant into the nerve for a long time.

Moreover, because the electrode collects neural signals from the outside of the nerve, the electrode cannot accurately read signals from the inside of the nerve and selectively obtain signals on nerve fiber level. Accordingly, the cuff electrode generally has the limited number of embedded electrodes, which is a factor limiting the neuroprosthetic or HMI applications.

To solve the problem of extraneural electrodes such as cuff electrodes, intrafascicular electrodes in which the electrodes are directly inserted into the nerve and through its fascicles may be used.

Typically, examples include a so-called transverse intra-fascicular multichannel electrode/longitudinal intra-fascicular electrode (TIME/LIFE) which thread type electrodes are inserted/penetrated into the nerve to read neural signals, a Utah probe electrode which has a plurality of probes arranged in a direction perpendicular to a plate body and are inserted into a corresponding nerve part, and a sieve electrode in which a thin plate type body that is inserted between the cut transected ends of the partially cut nerve and has sieve-holes with electrodes through which the nerve axons pass.

However with TIME/LIFE, it is difficult to place its few electrodes at a desired position in the nerve, resulting in low neural selectivity. Additionally, even after implantation, fixing of the electrodes is not easy, and the electrodes are likely to be moved the position by an external force, which is unfavorable for long-term implantation.

For the Utah electrode, many probes with relatively large spacings are inserted perpendicularly to the nerve, so overlapping nerve damage is very large. According to the manufacturing process of the electrode, the material of the probe is limited to silicon that is very stiff, causing continuous nerve damage in long-term implantation, and as a consequence of the foreign body response, the neural signal acquisition performance degrades.

Additionally, the sieve electrode has outstanding neural selectivity, allowing accurate mapping of neural signals corresponding to each electrode when the electrodes are embedded in each of the sieve-holes. However, because its implantation requires transection of the nerve, the damage to the nerve is very large.

To solve the problems of these conventional neural electrode structures, the applicant of the present application proposed a so-called "spiral neural probe structure" in the Patent Literature 1.

FIGS. 1 and 2 are conceptual diagrams of the spiral neural probe structure 1.

As shown in FIGS. 1 and 2, the neural probe structure 1 includes a body 10 of a flexible material, and a plurality of probes 20 connected to the body 10 and having electrodes to detect neural signals. The plurality of probes 20 is arranged at an interval along a lengthwise direction of the body 10.

The body 10 wraps the outer circumferential surface of a nerve N, and the plurality of probes 20 pierces the outer circumferential surface of the nerve N and is inserted into the nerve N.

As best shown in FIG. 1, the body 10 is connected to the nerve N, spirally surrounding the outer circumferential surface of the nerve N. When the body 10 surrounds the nerve N in a spiral shape, the plurality of probes 20 may be inserted into the nerve at different locations along the lengthwise direction of the nerve N. Accordingly, because invasion of the plurality of probes 20 does not concentration on a certain part, damage of the nerve N may be minimized.

Additionally, there is no occurrence in which the body 10 completely wraps part of the nerve N in the form of a closed loop by the spiral structure, thereby preventing a situation in which the nerve is compressed and the flow of blood is interrupted as with the conventional cuff electrode.

Additionally, as best shown in FIG. 2, when the body 10 is wrapped around the nerve N, the plurality of probes 20 may be radially arranged all over the inside of the nerve N. Thus, because the plurality of probes 20 is radially arranged all over the inside of the nerve N, a high density (number) of electrodes may be uniformly arranged within the nerve N. Accordingly, electrodes may be positioned linear most of the axons of the nerve. Therefore, it is possible to accurately acquire neural signals and improve spatial selectivity of measurement and stimulation site of the nerve.

However, the spiral neural probe structure 1 proposed by the earlier patent requires an operator to individually insert each of the plurality of probes 20 into the nerve in person. In the case of hand-operated insertion of the plurality of probes 20, it is difficult to guarantee the electrode insertion efficiency, and although the probes are inserted into the same spot, it is difficult that the probes are inserted in a direction perpendicular to the peripheral nerve surface. Additionally, the spiral neural probe structure 1 has a limitation where the duration of the surgical procedures increases in proportion to the number of probes, and nerve compression increases due to the individual insertion.

Consequently, a neural probe structure with a plurality of probes such as the spiral neural probe structure 1 needs an assistive instrument to facilitate the insertion of the plurality of probes into the nerve accurately and time efficiently.

RELATED LITERATURES

Patent Literatures (Patent Literature 1) Korean Patent No. 10-1700886

SUMMARY

The present disclosure is designed to solve the above-mentioned conventional problem, and therefore the present disclosure is directed to providing a probe insertion device that simultaneously inserts a plurality of probes into the peripheral nerve with correct posture, so that neural electrodes are uniformly inserted, thereby achieving the intended spatial resolution positioning of a neural probe structure.

To achieve the objective, according to an aspect of the present disclosure, there is provided a probe insertion device for a neural probe structure with a plurality of probes to simultaneously insert the plurality of probes into a nerve, the probe insertion device including a nerve holder to fix the nerve surrounding an outer circumference of the nerve, and a probe holder positioned outside in a radial direction of the nerve holder to fixedly support the probes surrounding a circumference of the nerve holder, wherein the probe holder includes a plurality of sections ("probe holder sections") arranged radially with respect to the nerve holder and moveable in a radial direction of the nerve holder, and the plurality of probe holder sections simultaneously moves the plurality of probes toward the nerve holder having fixed the nerve, so that the plurality of probes is simultaneously inserted into the nerve in a radial shape when viewed in a lengthwise direction of the nerve.

According to an embodiment, the neural probe structure includes a body of a flexible material to fix the plurality of probes such that the plurality of probes is arranged at an interval along a lengthwise direction, as the body surrounds the outer circumferential surface of the nerve, the plurality of probes pierces the outer circumferential surface of the nerve and is inserted into the nerve, and the probe holder has a continuous probe holder groove into which the body is inserted.

According to an embodiment, the body spirally surrounds the outer circumferential surface of the nerve, so that the plurality of probes is inserted into the nerve at different locations along the lengthwise direction of the nerve, and the probe holder groove is formed in a spiral shape along the lengthwise direction of the nerve.

According to an embodiment, the probe insertion device further includes a probe mover positioned outside in the radial direction of the probe holder, and the probe mover moves toward the nerve holder to press the plurality of probe holder sections so that the plurality of probe holder sections move and come together facing a center of the nerve.

According to an embodiment, the probe insertion device further includes a posture holder positioned between the probe holder and the probe mover, the posture holder includes a plurality of sections ("posture holder sections") arranged radially with respect to the nerve holder and moveable in the radial direction of the nerve holder, and one posture holder section is formed with a length throughout at least two probe holder sections.

According to an embodiment, the nerve holder includes two sections ("nerve holder sections") entirely surrounding the circumference of the nerve at a location where the nerve holder sections come together facing the nerve, and the probe mover includes two sections ("probe mover sections") entirely surrounding a circumference of the posture holder at a location where the probe mover sections come together facing the nerve.

According to an embodiment, the probe insertion device includes first forceps which presses the two probe mover sections up and down to move the two probe mover sections closer to each other, and second forceps connected to the nerve holder to force the two nerve holder sections together or apart.

According to an embodiment, the first forceps and the second forceps are driven with respect to one rotational axis.

According to an embodiment, each of the probe holder, the posture holder and the probe mover is moveably fixed to the nerve holder, a spring is installed between each of the probe holder, the posture holder and the probe mover, and the nerve holder, and the spring applies a force to the probe holder, the posture holder and the probe mover in a direction facing away from the nerve holder.

According to an embodiment, the probe is formed of a flexible material, an insertion assistive body corresponding to a shape of the probe is adhered to the probe, and the insertion assistive body is made of a biodegradable material which is biologically degraded in the nerve after a predetermined amount of time passes, and has a predetermined stiffness.

According to an embodiment, the probe holder has an insertion assistive pin which extends along a lengthwise direction of the probe in close contact with two surfaces of the probe.

According to an embodiment, the probe holder is replaceable with a probe punch, the probe punch includes a plurality of sections ("probe punch sections") corresponding to a shape of the probe holder, and each probe punch section has a punch pin to punch a hole in the nerve corresponding to a position of the probe.

BRIEF DESCRIPTION OF THE DRAWINGS

FIGS. 10A to 10C are operation diagrams illustrating the operation of the probe insertion device of FIGS. 3 and 4.

DETAILED DESCRIPTION

Figure 1:
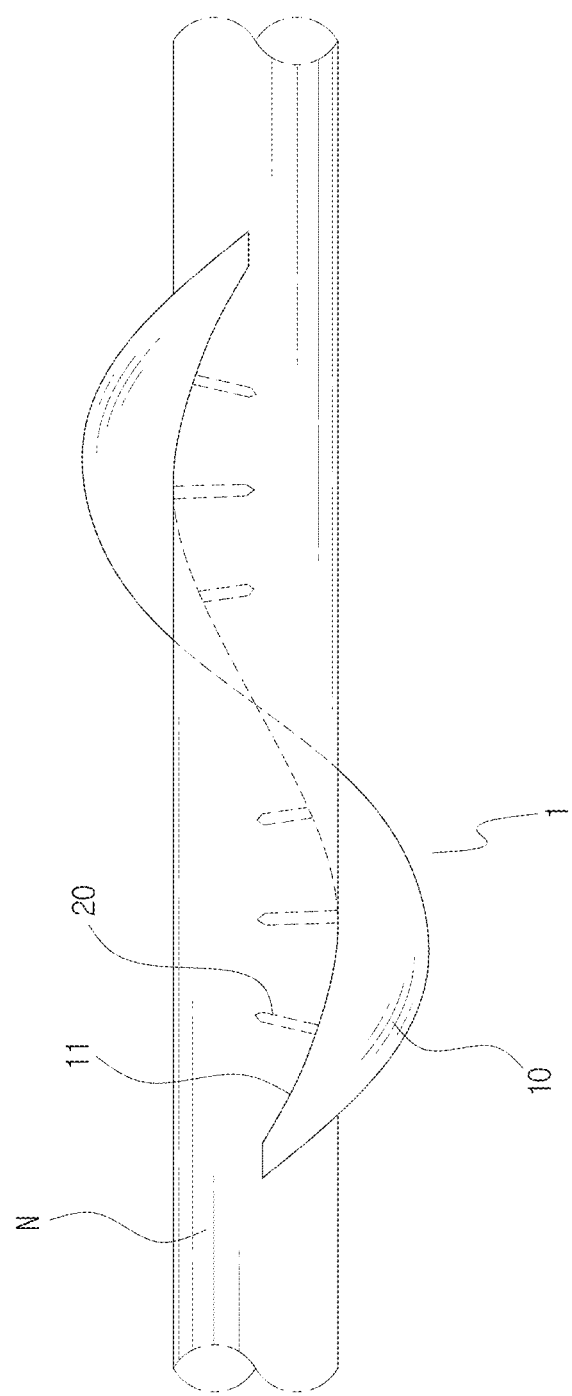
FIGS. 1 and 2 are conceptual diagrams of a spiral neural probe structure.

Hereinafter, preferred embodiments of the present disclosure will be described with reference to the accompanying drawings. The present disclosure is described with reference to the embodiments shown in the drawings, but it is described as one embodiment, and the technical spirit of the present disclosure and its key elements and operation are not limited thereby.

Figure 3:
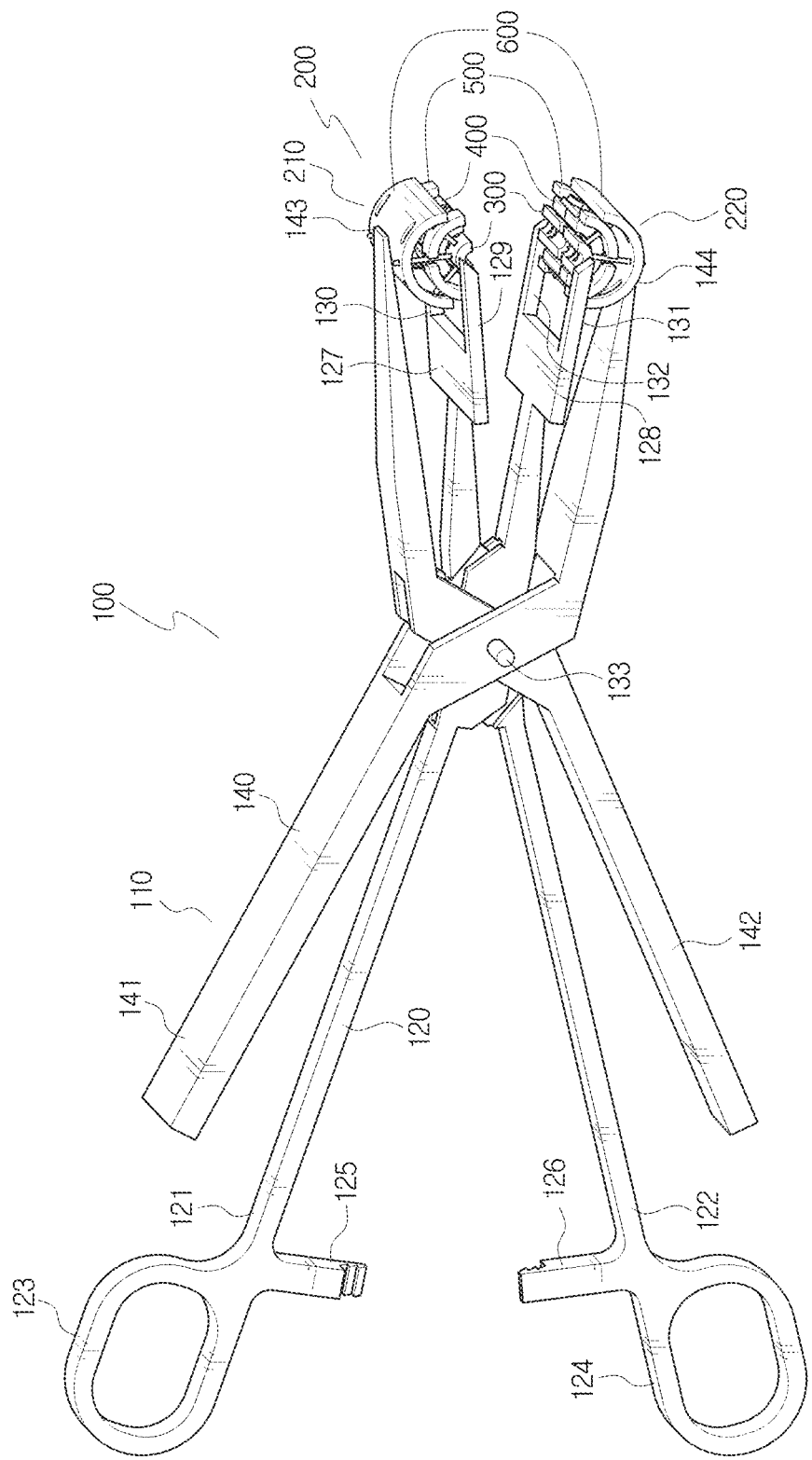
FIGS. 3 and 4 are perspective views of a probe insertion device according to an embodiment of the present disclosure.
Figure 4:
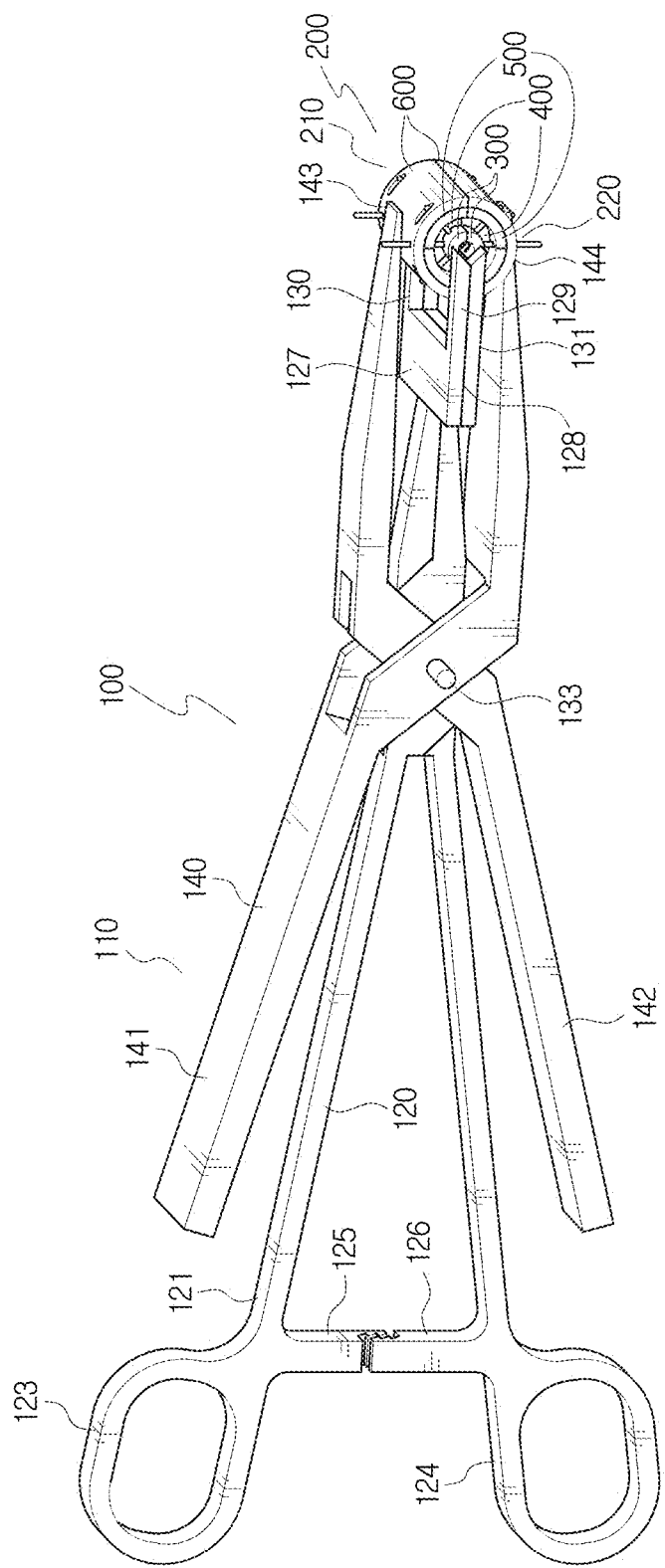

FIGS. 3 and 4 are perspective views of a probe insertion device 100 according to an embodiment of the present disclosure.

The probe insertion device 100 includes a probe insertion instrument 200 to fix a nerve N and a neural probe structure 1 to allow a plurality of probes 20 to be simultaneously inserted into the nerve N, and first forceps 110 and second forceps 120 to operate the probe insertion instrument 200.

As shown in FIGS. 3 and 4, the probe insertion instrument 200 includes an upper hemisphere 210 and a lower hemisphere 220 having a substantially symmetrical structure, and the upper hemisphere 210 and the lower hemisphere 220 may be forced together to form a cylindrical structure (FIG. 4) or may be forced apart (FIG. 3) by the operation of the second forceps 120.

Hereinafter, the structure of the probe insertion instrument 200 according to this embodiment is described in detail with reference to FIGS. 5 to 7.

Figure 5:
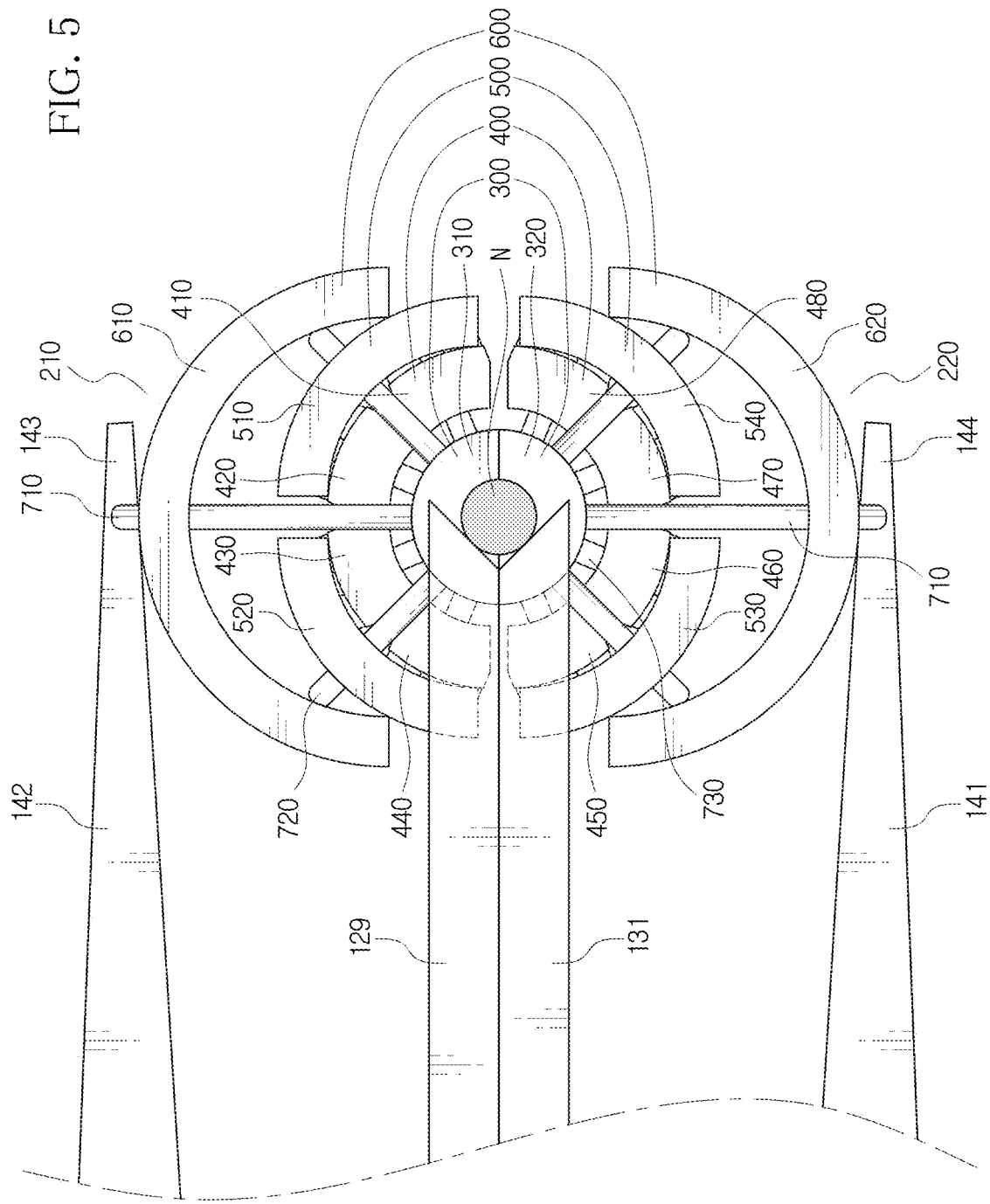
FIG. 5 is a side view of a probe insertion instrument of the probe insertion device of FIGS. 3 and 4.
Figure 6:
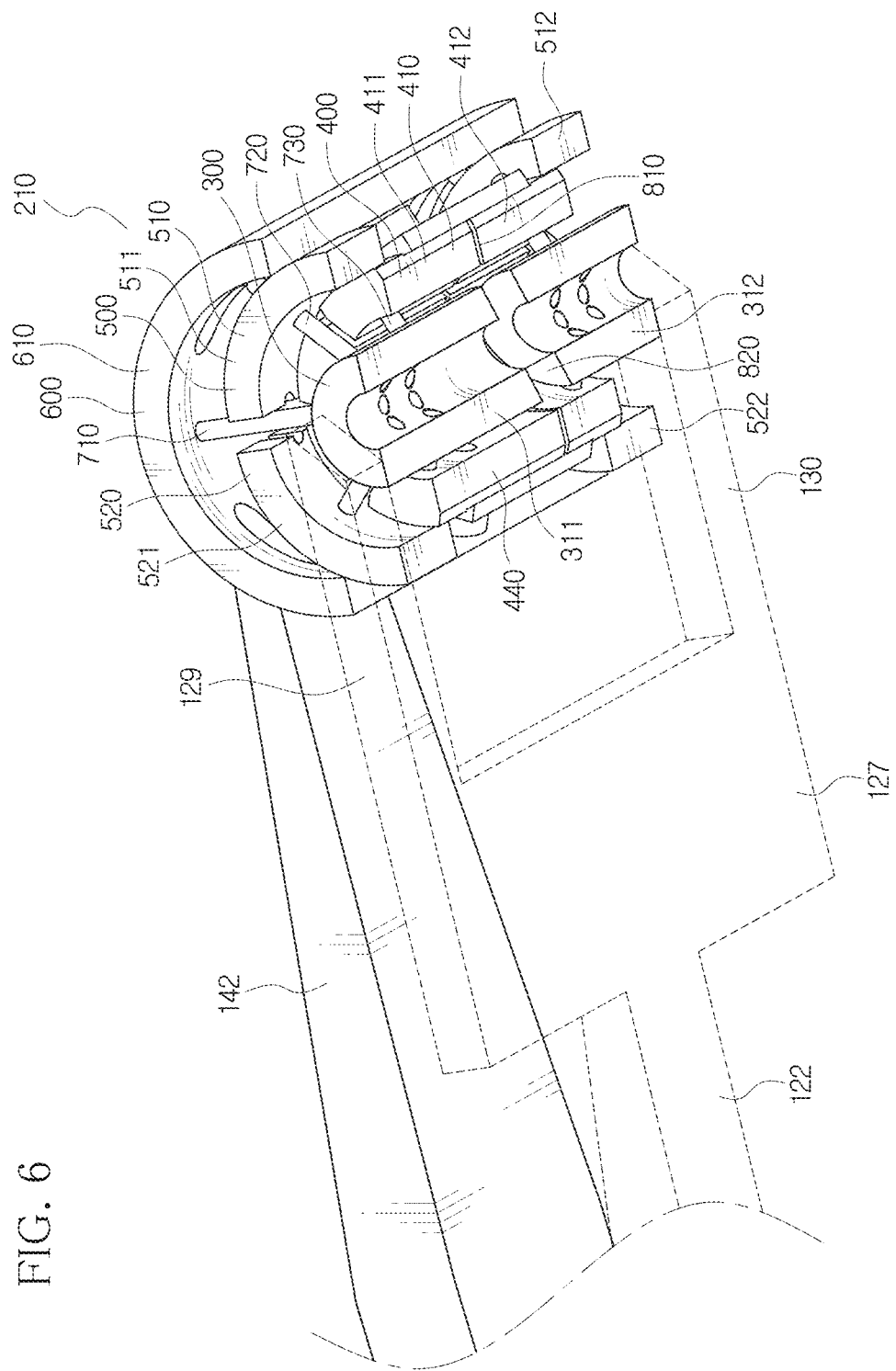
FIG. 6 is a partial perspective view of the probe insertion instrument of FIG. 5.
Figure 7:
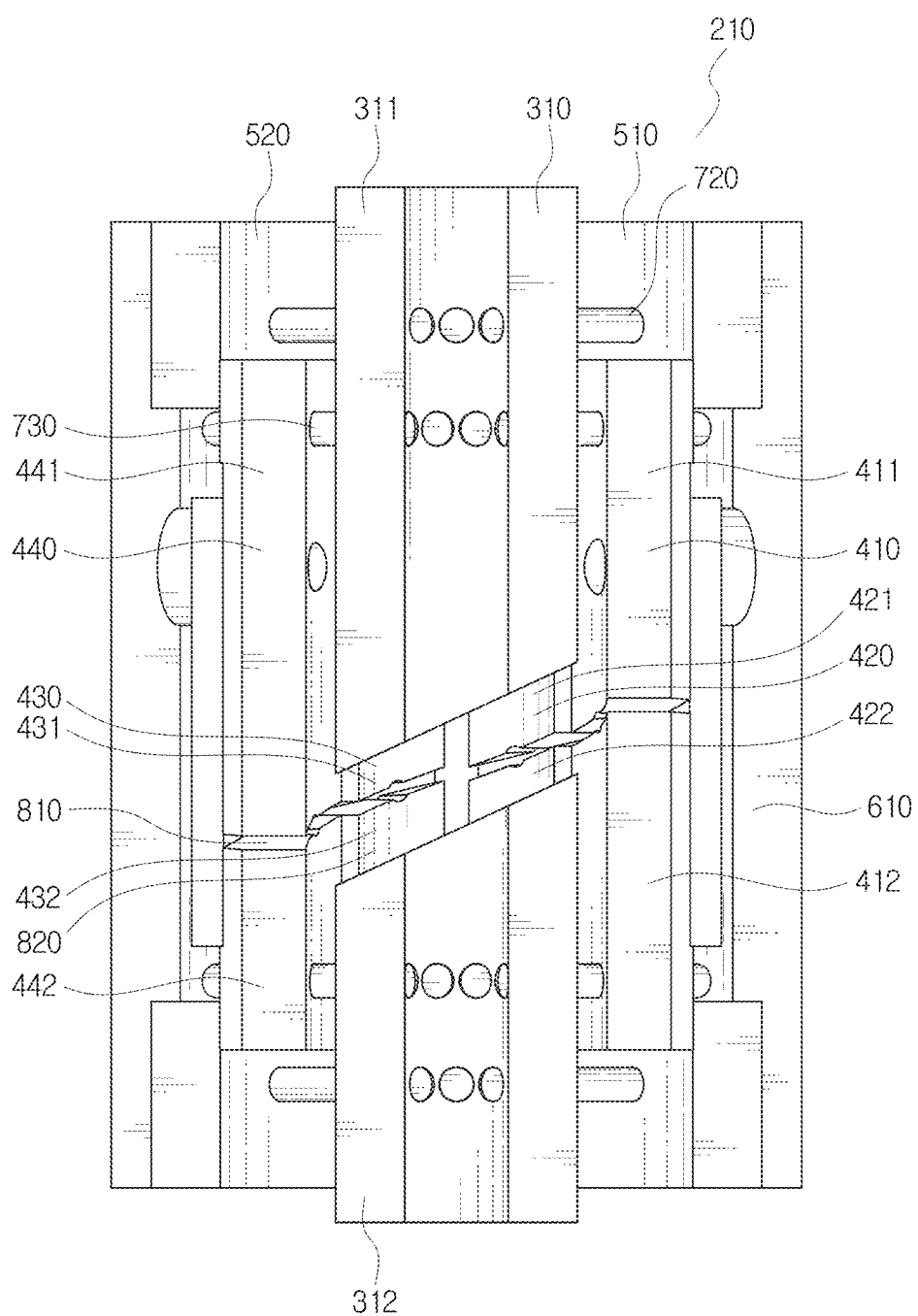
FIG. 7 is a partial bottom view of the probe insertion instrument of FIG. 5.

FIG. 5 is a side view of the probe insertion instrument 200, FIG. 6 is a perspective view of the upper hemisphere 210 of the probe insertion instrument 200, and FIG. 7 is a bottom view of the upper hemisphere 210 of the probe insertion instrument 200.

As shown in FIGS. 5 to 7, the probe insertion instrument 200 includes a nerve holder 300 to fix the nerve N surrounding the outer circumference of the nerve N, and a probe holder 400 positioned outside in the radial direction of the nerve holder 300 to fixedly support the neural probe structure 1 surrounding the circumference of the nerve holder 300. Additionally, the probe insertion instrument 200 includes a probe mover 600 positioned outside in the radial direction of the probe holder 400, and a posture holder 500 positioned between the probe holder 400 and the probe mover 600.

As shown in FIG. 5, the nerve holder 300 includes two nerve holder sections 310, 320 sufficiently and entirely surrounding the circumference of the nerve N at a location where they come together facing the nerve N. Referring to FIG. 6, each of the nerve holder sections 310, 320 is in the shape of a semicircular column, and when they come into close contact with each other, they form a circular column in shape and substantially entirely surround the circumference of the nerve N.

The probe holder 400 includes a plurality of sections ("probe holder sections") 410 to 480 arranged radially with respect to the nerve holder 300 and moveable in the radial direction of the nerve holder 300. According to this embodiment, the probe holder 400 is divided into 8 probe holder sections 410 to 480.

A total of 8 third extension bars 730 extend perpendicularly to the normal line of the nerve holder sections 310, 320 at an equivalent interval on the circumference of the nerve holder sections 310, 320. Each of the 8 probe holder sections 410 to 480 is connected to the third extension bar 730, and is formed such that they can move closer to or apart from the nerve holder 300 along the extension direction of the third extension bars 730.

Although not shown, the third extension bar 730 has a spring, and the spring applies a force to the probe holder sections 410 to 480 in a direction facing away from the nerve holder 300, and accordingly the probe holder sections 410 to 480 keep the position apart from the nerve holder 300.

The posture holder 500 includes a plurality of sections ("posture holder sections") 510 to 540 arranged radially with respect to the nerve holder 300 and moveable in the radial direction of the nerve holder 300. According to this embodiment, the posture holder 500 is divided into 4 probe holder sections 510 to 540.

A total of 4 second extension bars 720 are further formed in 90 degrees on the circumference of the nerve holder sections 310, 320, and the second extension bars 720 extend perpendicularly to the normal line of the nerve holder sections 310, 320. The second extension bars 720 are longer than the third extension bars 730.

Each of the 4 posture holder sections 510 to 540 is connected to the second extension bar 720, and is formed such that they can move closer to or apart from the nerve holder 300 along the extension direction of the second extension bars 720. Although not shown, the second extension bar 720 has a spring, and the spring applies a force to the posture holder sections 510 to 540 in a direction facing away from the nerve holder 300.

The probe mover 600 includes two probe mover sections 610, 620 divided in the same direction as the two nerve holder sections 310, 320 of the nerve holder 300. The probe mover sections 610, 620 substantially entirely surround the circumference of the posture holder 500 at a location where they come together facing the nerve N.

Two first extension bars 710 forming 180 degrees are further formed on the circumference of the nerve holder sections 310, 320, and the first extension bars 710 extend perpendicularly to the normal line of the nerve holder sections 310, 320. The first extension bars 710 are longer than the second extension bars 720.

Each of the two probe mover sections 610, 620 is connected to the first extension bar 710, and is formed such that they can move closer to or apart from the nerve holder 300 along the extension direction of the first extension bars 710. Although not shown, the first extension bar 710 has a spring, and the spring applies a force to the probe mover sections 610, 620 in a direction facing away from the nerve holder 300.

As described below, in the probe insertion device 100 according to this embodiment, while the plurality of probe holder sections 410 to 480 is fixing the plurality of probes 20 of the neural probe structure 1, the probe holder sections 410 to 480 simultaneously move to the nerve holder 300 having fixed the nerve N, so that the plurality of probes 20 is simultaneously inserted into the nerve N in a radial shape when viewed in the lengthwise direction of the nerve N (see FIG. 2).

Figure 2:
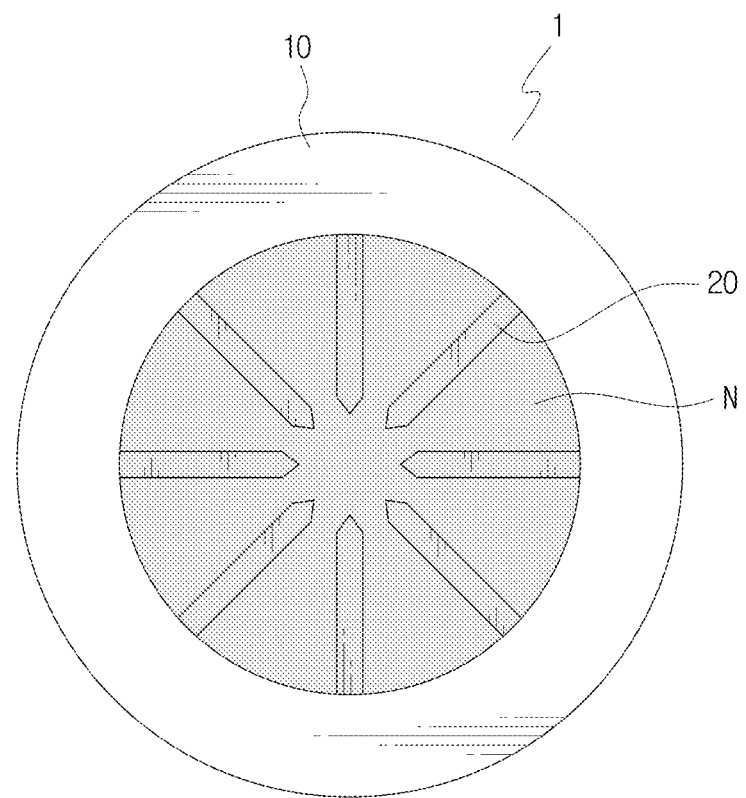

The probe insertion device 100 according to this embodiment is formed to install "the spiral neural probe structure 1" described in FIGS. 1 and 2 into the nerve N.

For the probe holder 400 to fix the neural probe structure 1, the probe holder 400 according to this embodiment has a continuous probe holder groove 810 in a spiral shape along the lengthwise direction of the nerve N, into which the body 10 of the neural probe structure 1 is inserted.

Figure 8:
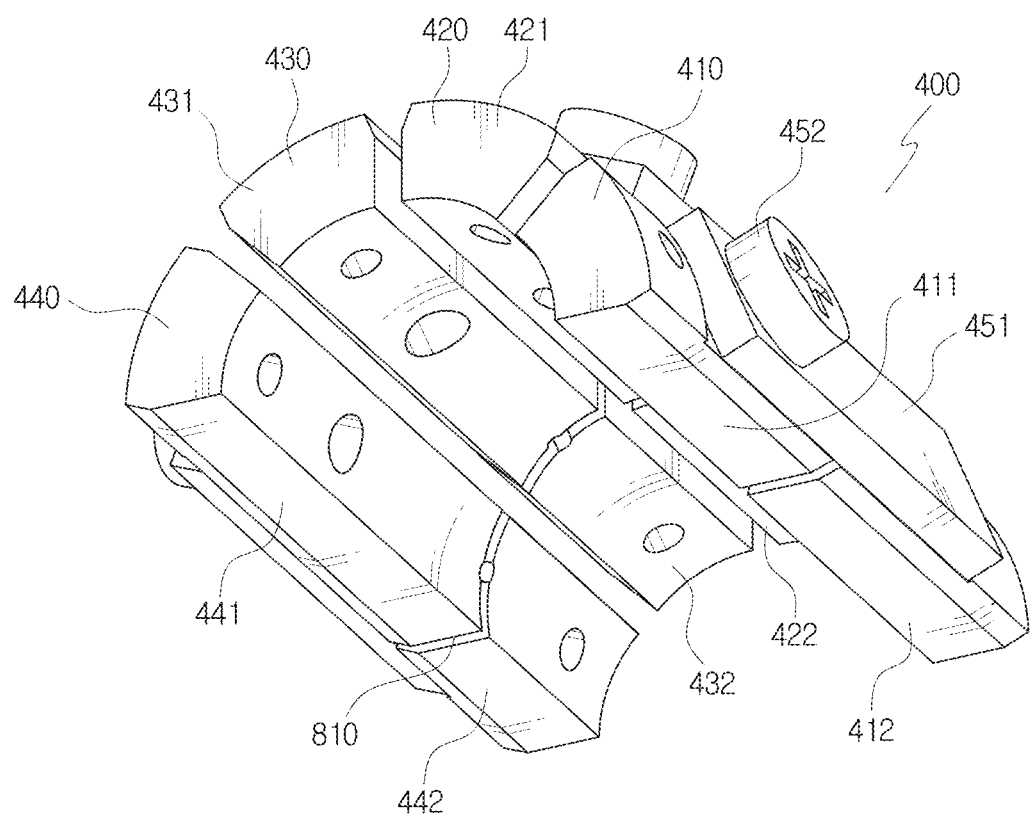
FIG. 8 is a perspective view of a probe holder of the probe insertion instrument of FIG. 5.

FIG. 8 is a perspective view of the probe holder 400 according to this embodiment. For convenience of description, FIG. 8 only shows 4 sections 410, 420, 430, 440 forming the upper hemisphere of the probe holder 400.

As shown in FIG. 8, the first probe holder section 410 of the probe holder 400 includes a front section 411 and a rear section 412. The front section 411 and the rear section 412 are spaced apart approximately as much as the thickness of the neural probe structure 1, forming a gap there between. The front section 411 and the rear section 412 are fixed with a predefined gap by a panel 451 and a bolt 452. The opposing cross sections of the front section 411 and the rear section 412 are formed as slant lines and parallel to each other.

Likewise, the second probe holder section 420 includes a front section 421 and a rear section 422, the third probe holder section 430 also includes a front section 431 and a rear section 432, and the fourth probe holder section 440 also includes a front section 441 and a rear section 442. Although not shown, each of the fifth to eighth probe holder sections 450 to 480 are also divided into a front section and a rear section.

The front section and the rear section forming each probe holder section have the same gap there between. However, as best shown in FIG. 7, the length of the front section and the rear section slightly differs for each probe holder section.

Referring to FIG. 7, for example, the front section 411 of the first probe holder section 410 is shorter than the front section 421 of the second probe holder section 420. The rear section 412 of the first probe holder section 410 is longer than the rear section 422 of the second probe holder section 420.

As described above, as the front section becomes longer from the first probe holder section 410 to the eighth probe holder section 480 and the ends of the front section and the rear section of each probe holder section are formed in parallel as slant lines, the probe holder 400 has the continuous spiral probe holder groove 810.

Figure 9:
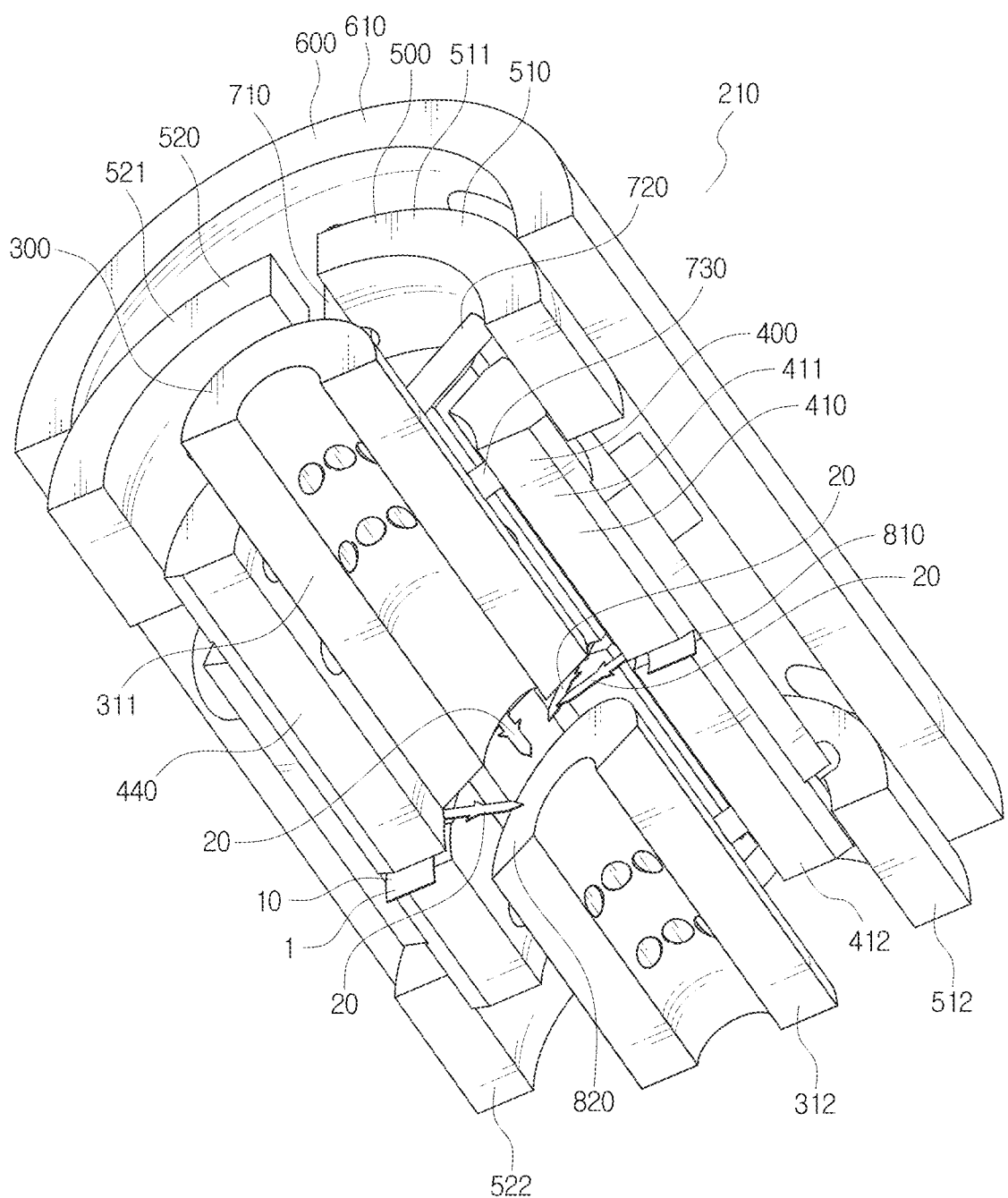
FIG. 9 shows that a neural probe structure is fixed in a probe holder groove of the probe insertion instrument of FIG. 5.

FIG. 9 shows that the neural probe structure 1 is fixed in the probe holder groove 810. It should be understood that the neural probe structure 1 intended in the specification include all embodiments stated in Korean Patent Application No. 10-2015-0105248.

As shown in FIG. 9, the body 10 of the neural probe structure 1 is received in the probe holder groove 810, and the plurality of probes 20 is arranged facing the inner diameter of the probe holder 400. As shown in FIG. 9, by the structure of the spiral probe holder groove 810, the plurality of probes 20 is arranged at different locations along the lengthwise direction of the nerve N (i.e., the lengthwise direction of the probe insertion device 100) and their ends are arranged facing different directions.

As the plurality of probe holder sections 410 to 480 of the probe holder 400 is spaced apart radially from the nerve holder 300 by the spring, the flexible, elastic body 10 is slightly extended and inserted into the probe holder groove 810 at the initial installation location as shown in FIG. 9.

As shown in FIG. 7, a small guide groove is formed at the ends of the front section and the rear section of each probe holder section. When the probe 20 thicker than the body 10 is positioned at the guide groove, the neural probe structure 1 may be fixed in the probe holder groove 810 and each probe 20 may be placed right in an installation position.

By the action of the guide groove, it is possible to prevent the probe 20 from moving away from an expected position due to the movement of the neural probe structure 1 in the circumferential direction of the probe insertion device 100 during the operation of the probe insertion device 100.

Referring back to FIGS. 6 and 7, to allow the outer circumferential surface of the nerve N to be exposed to the probe 20 of the neural probe structure 1 fixed to the probe holder 400, the first nerve holder section 310 of the nerve holder 300 is divided into a front section 311 and a rear section 312 spaced apart from each other.

The front section 311 is fixed to a front tip 129 of two branches of a fork 127 formed at the end of the second forceps 120, and the rear section 312 is fixed to a front tip 130, and thus the two sections 311, 312 are fixed apart at a predefined interval.

Similar to the front section and the rear section of the probe holder section, the ends of the front section 311 and the front section 312 are formed as slant lines and spaced apart from each other to form a spiral nerve holder slit 820 in the same direction as the probe holder groove 810.

As shown in FIG. 9, the probe 20 fixed to the probe holder 400 extends through the nerve holder slit 820 toward the outer circumferential surface of the nerve N exposed to the nerve holder slit 820. To prevent the interference from occurring while the probe 20 is inserted into the nerve, the width of the nerve holder slit 820 is larger than the width of the probe holder groove 810.

Meanwhile, as shown in FIGS. 6 and 7, both the posture holder sections 510, 520 of the posture holder 500 include front panels 511, 521 and rear panels 512, 522 positioned at the front and rear of the probe holder 400, to create a space in which the panel 451 and the bolt 452 of the probe holder will be positioned. Meanwhile, each posture holder section 510, 520 has a length throughout at least two probe holder sections.

Hereinafter, a detailed operation of the probe insertion device 100 is described.

Referring back to FIGS. 3 and 4, the probe insertion instrument 200 operates by the first forceps 110 and the second forceps 120.

The second forceps 120 includes a first arm 121 and a second arm 122 formed in the shape of letter "x" with respect to a rotational axis 133.

Handles 123, 124 in which a user puts fingers to grip are formed at the rear end of the first arm 121 and the second arm 122. Binders 125, 126 that extend facing each other are formed in front of the handles 123, 124. Toothed binder parts that are engaged with each other are formed at the end of the binders 125, 126, and when the binder parts are engaged with each other, the first arm 121 and the second arm 122 are fixed in a contracted state.

Forks 127, 128 that are branched into two are formed at the front end of the first arm 121 and the second arm 122. The front tip 129 of the second fork 127 is fixed to the front section 311 of the first nerve holder section 310, and the rear tip 130 is fixed to the rear section 312 of the first nerve holder section 310.

A front tip 131 of the first fork 128 is fixed to the front section of the second nerve holder section 320, and a rear tip 132 is fixed to the rear section of the second nerve holder section 320.

When the first arm 121 and the second arm 122 are contracted or spread, the two nerve holder sections 310 of the nerve holder 300 move closer to each other or apart from each other, and accordingly the upper hemisphere 210 and the lower hemisphere 220 of the probe insertion instrument 200 entirely move closer to each other or apart from each other.

The first forceps 110 includes a third arm 141 and a fourth arm 142 formed in the shape of letter "x" with respect to the same rotational axis 133 as the second forceps 120. As the first forceps 110 operates with respect to the same rotational axis 133 as the second forceps 120, the structure of the device may be simplified.

A front end 143 of the fourth arm 142 comes into contact with the first probe mover section 610 on the top of the first probe mover section 610, and a front end 144 of the third arm 141 comes into contact with the second probe mover section 620 on the bottom of the second probe mover section 620.

When the user holds the rear end parts of the third arm 141 and the fourth arm 142 and contracts the third arm 141 and the fourth arm 142, the front end 144 of the third arm 141 and the front end 143 of the fourth arm 142 press the two probe mover sections 610, 620 up and down respectively to move the probe mover sections 610, 620 closer to each other.

FIGS. 10A to 10C are operation diagrams illustrating the operation of the probe insertion device 100.

As shown in FIG. 10A, after the user positions the nerve N between the probe insertion instrument 200 where the upper hemisphere 210 and the lower hemisphere 220 are spaced apart as shown in FIG. 3, the user contracts the first arm 121 and the second arm 122 of the second forceps 120 to bring the two forks 127, 128 into close contact, and engages the toothed binder parts to fix the first arm 121 and the second arm 122.

The nerve N is firmly fixed while surrounded by the two nerve holder sections 310, 320 of the nerve holder 300.

In this instance, as shown in FIG. 10A, the probe holder 400 is placed in a state that it is spread radially by the action of the spring.

Subsequently, as shown in FIG. 10B, the third arm 141 and the fourth arm 142 of the first forceps 110 are contracted to compress the probe mover 600.

The probe mover sections 610, 620 of the probe mover 600 move closer to each other facing the nerve holder 300 to compress the posture holder 500 and the probe holder 400. Accordingly, each probe holder section 410 to 480 of the probe holder 400 simultaneously moves and comes together facing the center of the nerve N, and the probe 20 fixed to the probe holder 400 is implanted into the nerve N through the nerve holder slit 820.

According to this embodiment, as shown in FIG. 10B, when the two probe mover sections 610, 620 come into close contact with each other, the posture holder 500 is received in the inside of the probe mover 600, the probe holder 400 is received in the inside of the posture holder 500, and eventually the probe insertion instrument 200 has substantially a cylindrical structure with the probe mover 600 on the outermost.

The probe mover sections 610, 620 roughly in the shape of letter "C" make a linear movement so that the probe holder sections 410 to 480 come together at the center of the nerve, and in this instance, in the absence of the posture holder 500, the probe holder sections 410 to 480 cannot move simultaneously. In other words, when the first probe mover section 610 moves, the first probe holder section 410 and the fourth probe holder section 440 positioned on two sides move first, and after the first probe mover section 610 moves further downward, the second probe holder section 420 and the third probe holder section 430 move.

In this process, each probe holder section 410 to 440 may shake, failing to extend straight along the third extension bars 730, which makes it difficult to simultaneously insert the probes 20 with correct posture.

According to this embodiment, one posture holder section 510 is supported on the two probe holder sections 410, 420, and the two posture holder sections 510, 520 come into contact with the probe mover section 610.

Accordingly, when the probe mover section 610 moves down, the two posture holder sections 510, 520 simultaneously move and come together facing the center of the nerve N, and as the two posture holder sections 510, 520 simultaneously move, the four probe holder sections 410 to 440 in contact with them simultaneously move.

Accordingly, all the probes 20 may be simultaneously inserted into the nerve N by one motion. Additionally, each probe holder section 410 to 440 moves in a straight line along the third extension bars 730 without a shake, so that the probes 20 may be accurately inserted perpendicularly to the outer circumferential surface of the nerve N.

After the probes 20 are inserted into the nerve N, the first arm 121 and the second arm 122 of the second forceps 120 are spread to force the two forks 127, 128 apart as shown in FIG. 10C.

The neural probe structure 1 fixed to the nerve N is left in the nerve N, and the probe insertion instrument 200 may be split into the upper hemisphere 210 and the lower hemisphere 220, and move away from the nerve N.

According to the probe insertion device 100 according to this embodiment, the plurality of probes 20 may be inserted into a correct position of the nerve N by one instrument, thereby eliminating the inconvenience of individually inserting each probe into the nerve.

Meanwhile, to minimize damage of the nerve N and use the neural probe structure 1 for a long time, the body of the probe 20 is preferably formed of a flexible material that does not have high stiffness like that of silicon.

Accordingly, the probe insertion device 100 according to this embodiment may include a punch assistive means to assist the flexible probe 20 in easily punching a hole in the nerve N.

Figure 11:
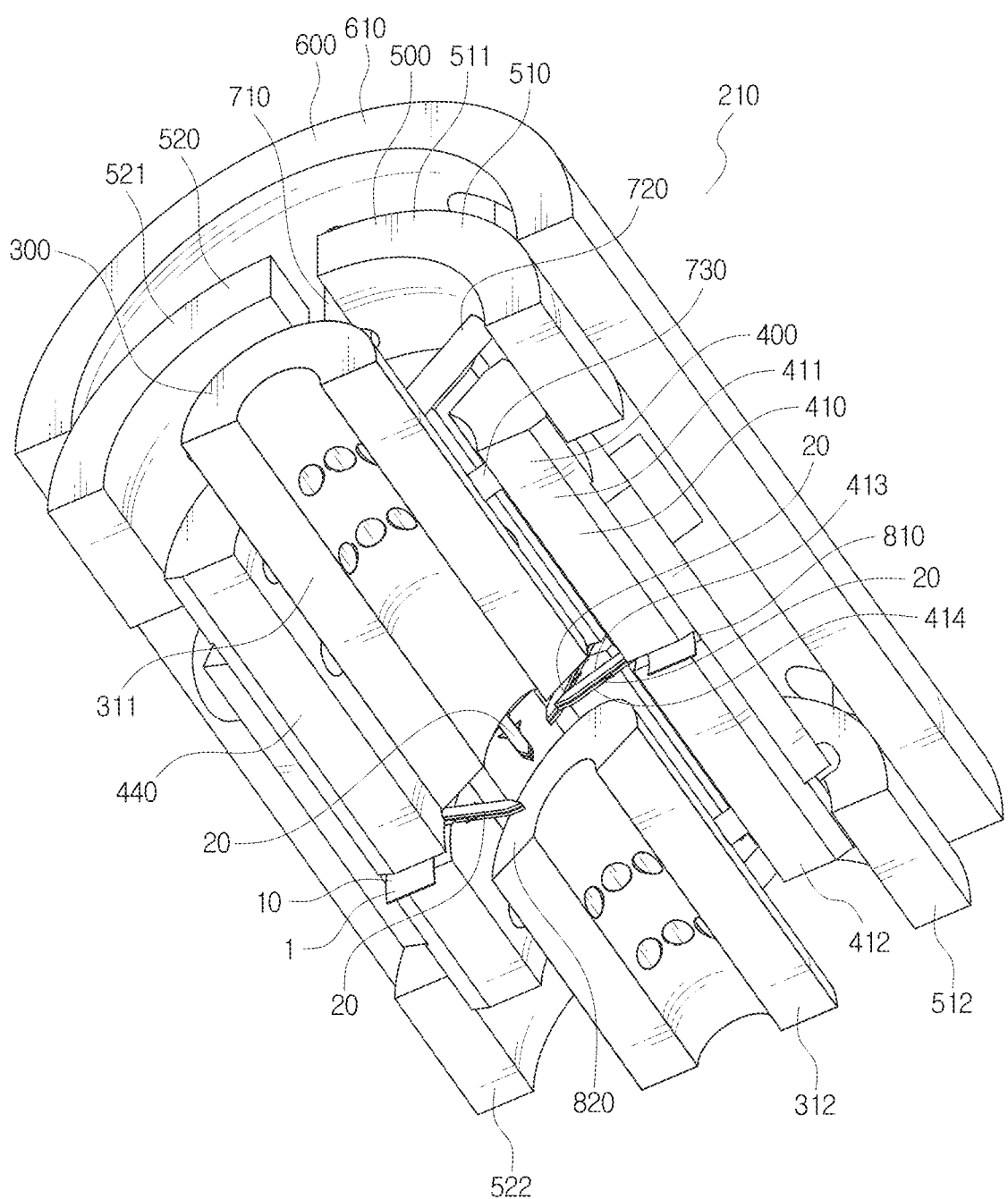
FIGS. 11 and 12 show a probe insertion device including a punch assistive means according to an embodiment.
Figure 12:
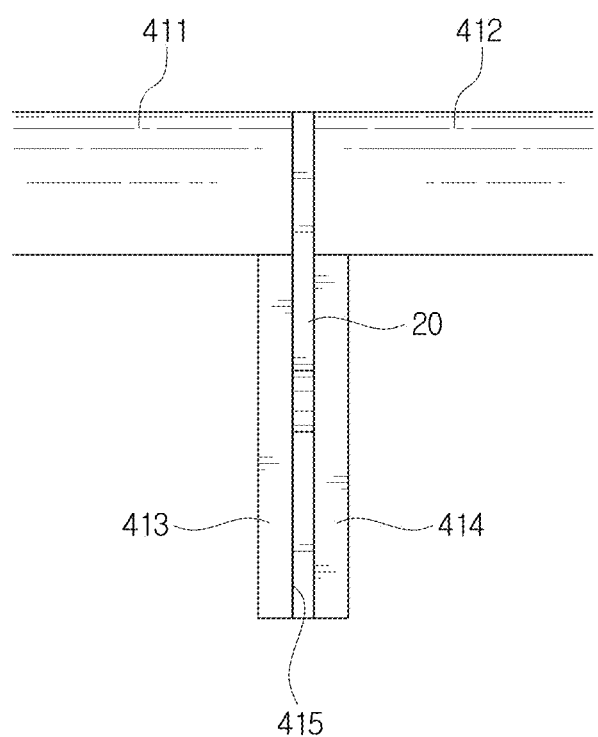

FIGS. 11 and 12 show the probe insertion device 100 including the punch assistive means according to an embodiment.

As shown in FIGS. 11 and 12, in the probe insertion device 100 according to this embodiment, the probe holder 400 includes, as the punch assistive means, insertion assistive pins 413, 414 that come into close contact with two surfaces of the probe 20 and extend along the lengthwise direction of the probe 20.

As best shown in FIG. 12, each of the two insertion assistive pins 413, 414 extends with a gap corresponding to the thickness of the probe 20 from the front section 411 and the rear section 412 of the probe holder section. The two insertion assistive pins 413, 414 have substantially a shape corresponding to the probe 20. However, the two insertion assistive pins 413, 414 have a smooth side surface with no spike dissimilar to the probe 20 (see FIG. 9).

As the probe holder section 410 moves, the two insertion assistive pins 413, 414 having stiffness run through the nerve N together with the probe 20, and when the probe insertion instrument 200 moves away from the nerve N as shown in FIG. 10C, the insertion assistive pins 413, 414 slip away from the nerve N together. In this instance, the probe 20 is left after it is inserted into the nerve N.

Figure 13:
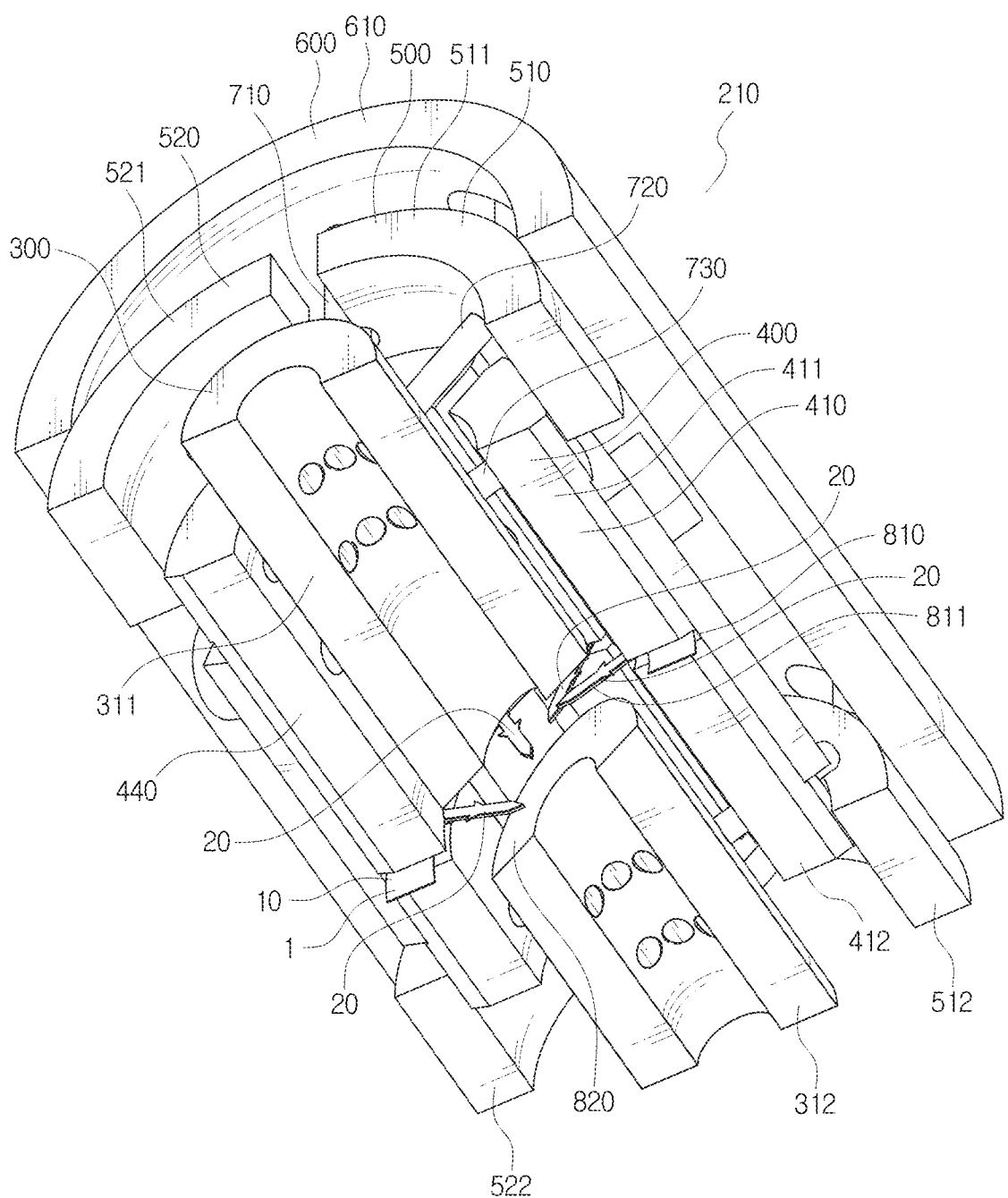
FIGS. 13 and 14 show a probe insertion device including a punch assistive means according to another embodiment.
Figure 14:
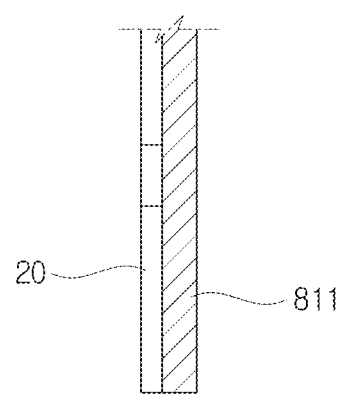

FIGS. 13 and 14 show the probe insertion device 100 including the punch assistive means according to another embodiment.

As shown in FIGS. 13 and 14, the probe insertion device 100 according to this embodiment includes, as the punch assistive means, an insertion assistive body 811 that is adhered to at least one surface of the probe 20.

The insertion assistive body 811 is formed in a shape corresponding to the probe 20. The insertion assistive body 811 according to this embodiment is formed of a biodegradable material (for example, silk, polyethylene glycol (PEG), polyvinyl alcohol (PVA), dextran, and maltose) that is biologically degraded in the nerve N after a predetermined amount of time passes. Moreover, the insertion assistive body 811 is formed with a predetermined stiffness that is greater than the probe 20.

As the probe holder section 410 moves, the insertion assistive body 811 having stiffness runs through the nerve N together with the probe 20, and after the probe insertion instrument 200 moves away from the nerve N as shown in FIG. 10C, the insertion assistive body 811 is still left in the nerve N together with the probe 20. However, after a predetermined amount of time passes, the insertion assistive body 811 is decomposed and disappears, and the probe 20 restores its unique flexibility.

Figure 15:
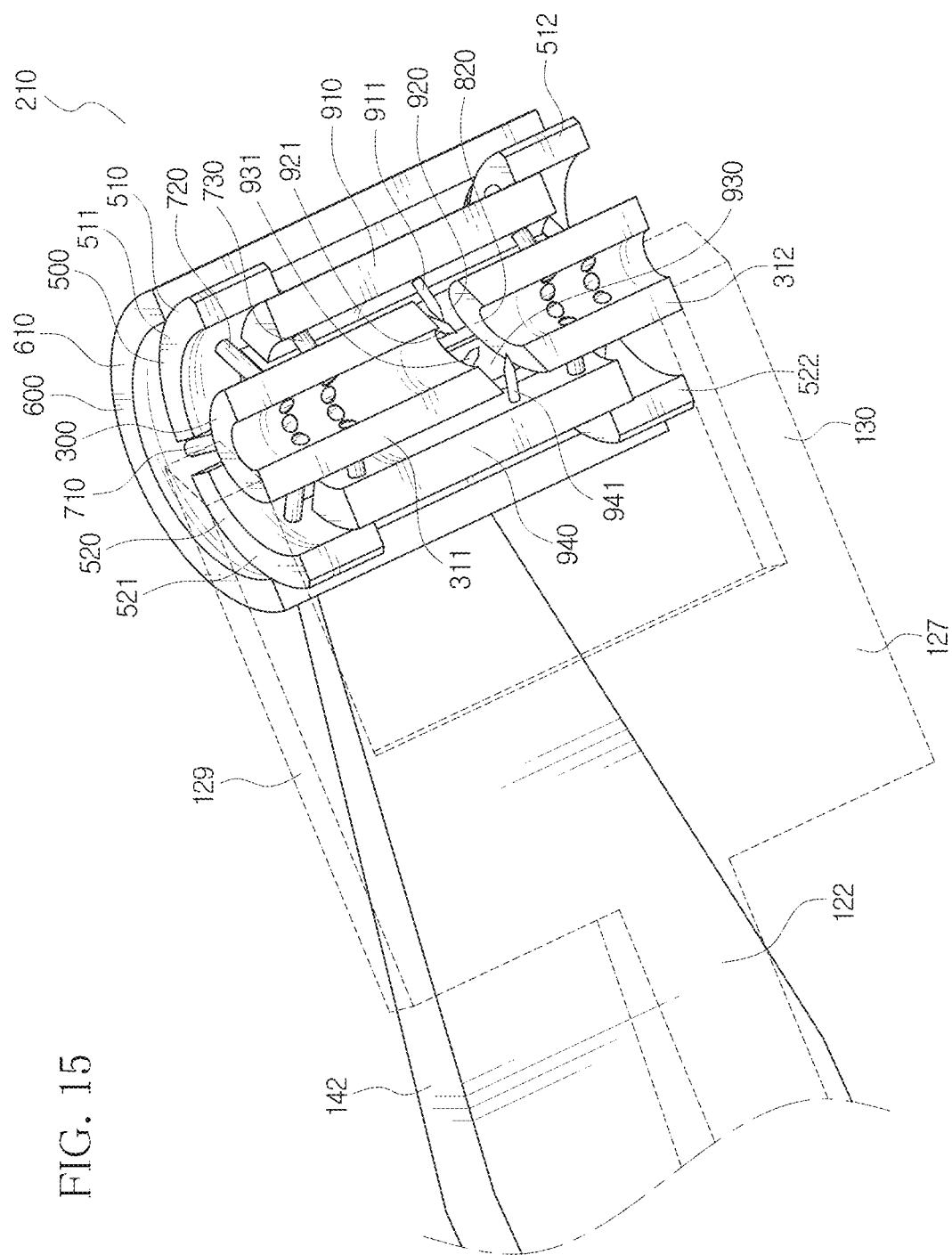
FIGS. 15 and 16 show a probe insertion device including a punch assistive means according to still another embodiment.
Figure 16:
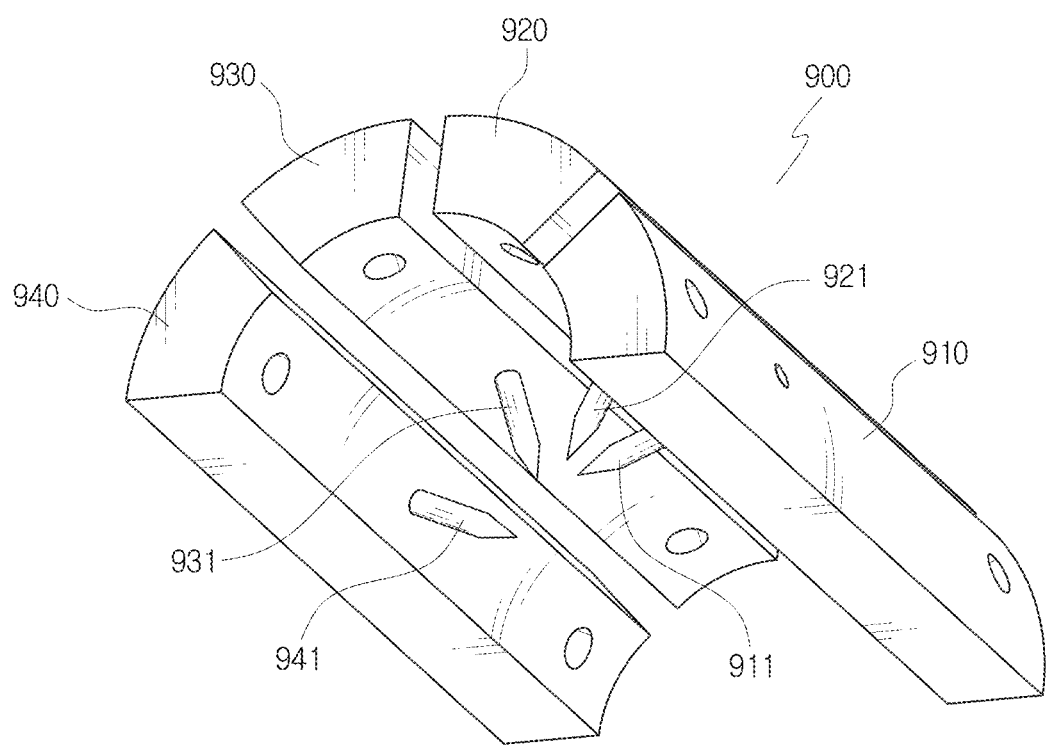

FIGS. 15 and 16 show the probe insertion device 100 including the punch assistive means according to still another embodiment.

As shown in FIG. 15, the probe insertion device 100 according to this embodiment includes, as the punch assistive means, a probe punch 900 that may replace the probe holder 400.

As shown in FIG. 16, the probe punch 900 includes a plurality of sections ("probe punch sections") 910 to 940 corresponding to the shape of the probe holder 400. FIG. 16 only shows four probe punch sections corresponding to the upper hemisphere 210, and it will be understood that 8 probe punch sections are, in effect, formed corresponding to the probe holder sections.

As shown in FIG. 16, each probe punch section 910, 920, 930, 940 has a punch pin 911, 921, 931, 941 to punch a hole in the nerve N corresponding to the position of the probe 20 fixed to the probe holder section.

In case that the probe punch 900 is connected to the probe insertion device 100 in place of the probe holder 400, when the operation of FIGS. 10A to 10C is performed, the nerve N has a hole pre-punched at a location into which the probe 20 is to be inserted.

Again, the probe holder 400 is connected to the probe insertion device 100 in place of the probe punch 900, and the operation of FIGS. 10A to 10C is performed to fix the neural probe structure 1 to the nerve N. In this instance, as the probe 20 is inserted into the hole pre-punched in the nerve N, the flexible probe 20 may be inserted into the nerve N without much difficulty.

Of course, without replacing the probe holder 400 and the probe punch 900 for one probe insertion device 100, two probe insertion devices to which the probe holder 400 and the probe punch 900 are each connected may be prepared, and the two probe insertion devices may operate in a sequential order to fix the neural probe structure 1 to the nerve N.

What is claimed is:

1. A probe insertion device for a neural probe structure with a plurality of probes, the probe insertion device being configured to simultaneously insert the plurality of probes into a nerve, the probe insertion device comprising:
    a nerve holder configured to surround an outer circumference of the nerve and to fix the nerve;
    a probe holder positioned outside of the nerve holder in a radial direction and surrounding a circumference of the nerve holder, the probe holder being configured to fixedly support the plurality of probes; and
    a probe mover positioned outside of the probe holder in the radial direction,
    wherein
    the probe holder includes a plurality of probe holder sections arranged radially with respect to the nerve holder and moveable in the radial direction,
    the plurality of probe holder sections simultaneously moves the plurality of probes toward the nerve holder having fixed the nerve, so that the plurality of probes is simultaneously inserted into the nerve in a radial shape when viewed in a lengthwise direction of the nerve, and
    the probe mover moves toward the nerve holder to press the plurality of probe holder sections so that the plurality of probe holder sections move and come together facing a center of the nerve.

2. The probe insertion device according to claim 1, wherein the neural probe structure includes a body of a flexible material to fix the plurality of probes such that the plurality of probes is configured to be arranged at an interval along a lengthwise direction of the nerve,
    the plurality of probes is configured to pierce the outer circumferential surface of the nerve and to be inserted into the nerve as the body surrounds an outer circumferential surface of the nerve, and
    the probe holder has a continuous probe holder groove into which the body is inserted.

3. The probe insertion device according to claim 2, wherein the body is configured to spirally surround the outer circumferential surface of the nerve, so that the plurality of probes is spirally inserted into the nerve at different locations along the lengthwise direction of the nerve, and
    the probe holder groove is formed in a spiral shape along the lengthwise direction of the nerve.

4. The probe insertion device according to claim 1, further comprising a posture holder positioned between the probe holder and the probe mover, wherein
    the posture holder includes a plurality of posture holder sections arranged radially with respect to the nerve holder and moveable in the radial direction, and
    one posture holder section is formed with a length throughout at least two probe holder sections.

5. The probe insertion device according to claim 4, wherein the nerve holder includes two nerve holder sections configured to entirely surround the circumference of the nerve at a location where the nerve holder sections come together facing the nerve, and
    the probe mover includes two probe mover sections configured to entirely surround a circumference of the posture holder at a location where the probe mover sections come together facing the nerve.

6. The probe insertion device according to claim 5, further comprising:
    first forceps which presses the two probe mover sections up and down to move the two probe mover sections closer to each other; and second forceps connected to the nerve holder to force the two nerve holder sections together or apart, the second forceps having a first arm and a second arm configured to rotate about a rotational axis, and the first forceps having a third arm and a fourth arm configured to rotate about the rotational axis.

7. The probe insertion device according to claim 5, wherein each of the probe holder, the posture holder and the probe mover is moveably fixed to the nerve holder, a spring is installed between each of the probe holder, the posture holder and the probe mover, and the nerve holder, and the spring applies a force to the probe holder, the posture holder and the probe mover in a direction facing away from the nerve holder.

8. The probe insertion device according to claim 1, wherein the probe is formed of a flexible material, an insertion assistive body corresponding to a shape of the probe is adhered to the probe, and the insertion assistive body is made of a biodegradable material which is biologically degraded in the nerve after a predetermined amount of time passes, and has a predetermined stiffness.

9. The probe insertion device according to claim 1, wherein the probe holder has an insertion assistive pin which extends along a lengthwise direction of the probe in close contact with two surfaces of the probe.

10. The probe insertion device according to claim 1, wherein the probe holder is replaceable with a probe punch, the probe punch includes a plurality of probe punch sections corresponding to a shape of the probe holder, and each probe punch section has a punch pin configured to punch a hole in the nerve corresponding to a position of the probe.

11. The probe insertion device according to claim 1, further comprising:

a posture holder positioned separately from and radially outside the probe holder, between the probe holder and the probe mover;

wherein the posture holder comprises a plurality of posture holder sections arranged radially with respect to the nerve holder and moveable in the radial direction.

12. The probe insertion device according to claim 11, wherein the probe mover comprises a first probe mover section and a second probe mover section, each having substantially a "C" shape and being disposed separately from and radially outside the posture holder so as to substantially entirely surround a circumference of the posture holder.

13. The probe insertion device according to claim 12, further comprising a plurality of extension bars extending radially about a circumference of the nerve holder, between the nerve holder and the probe mover.

* * * * *